United States Patent
Aharoni

(10) Patent No.: US 10,548,713 B2
(45) Date of Patent: Feb. 4, 2020

(54) INTRAOCULAR LENS INCLUDING SCLERAL ENGAGEMENT PORTION

(71) Applicant: Visioncare, Inc., Saratoga, CA (US)

(72) Inventor: Eli Aharoni, Tel Aviv (IL)

(73) Assignee: Visioncare, Inc., Saratoga, CA (US)

( * ) Notice: Subject to any disclaimer, the term of this patent is extended or adjusted under 35 U.S.C. 154(b) by 155 days.

(21) Appl. No.: 15/603,705

(22) Filed: May 24, 2017

(65) Prior Publication Data

US 2018/0338825 A1    Nov. 29, 2018

(51) Int. Cl.
*A61F 2/16* (2006.01)

(52) U.S. Cl.
CPC ........ *A61F 2/16* (2013.01); *A61F 2002/1681* (2013.01); *A61F 2220/0008* (2013.01)

(58) Field of Classification Search
CPC ...... A61F 2220/0008; A61F 2250/0018; A61F 2/1613; A61F 2/16; A61F 2002/1683; A61F 2002/1681; A61L 27/16
See application file for complete search history.

(56) References Cited

U.S. PATENT DOCUMENTS

| 5,006,123 A | 4/1991 | Soll et al. |
| 7,736,389 B1 | 6/2010 | Damiano |
| 2006/0069433 A1* | 3/2006 | Nun .................. A61F 2/1613 623/6.45 |
| 2006/0235428 A1 | 10/2006 | Silvestrini |
| 2016/0278913 A1 | 9/2016 | Aharoni et al. |

FOREIGN PATENT DOCUMENTS

| CN | 102090946 | 6/2011 | |
| EP | 3 158 974 | * 4/2017 | ............... A61F 2/16 |
| GB | 2242835 | 10/1991 | |
| JP | 2007-007332 | 1/2007 | |
| JP | 6045659 | 12/2016 | |
| RU | 2367380 | 9/2009 | |
| WO | 2011/021225 | 2/2011 | |
| WO | WO 2015/194335 | * 12/2015 | ............... A61F 2/16 |
| WO | WO 216/159910 | * 10/2016 | ............... A61F 2/16 |
| WO | 2016/182520 | 11/2016 | |

OTHER PUBLICATIONS

Notice of Allowance dated Sep. 12, 2018, which issued during the prosecution of U.S. Appl. No. 15/030,803.
An English translation of an Office Action dated Jul. 24, 2018 which issued during the prosecution of Japanese Patent Application No. 2016-551109.
European Search Report dated Nov. 6, 2018, which issued during the prosecution of Applicant's European App No. 18173017.7.

* cited by examiner

*Primary Examiner* — David H Willse
*Assistant Examiner* — Tiffany P Shipmon
(74) *Attorney, Agent, or Firm* — Fish & Richardson P.C.

(57) ABSTRACT

An intraocular lens including a lens portion and a haptics portion, the haptics portion including a scleral engagement portion including an elongate scleratomy transversing portion and a scleral engagement fixation portion, located at an intermediate location along a length of the elongate scleratomy transversing portion, preventing disengagement of the scleratomy transversing portion from a sclera.

12 Claims, 22 Drawing Sheets

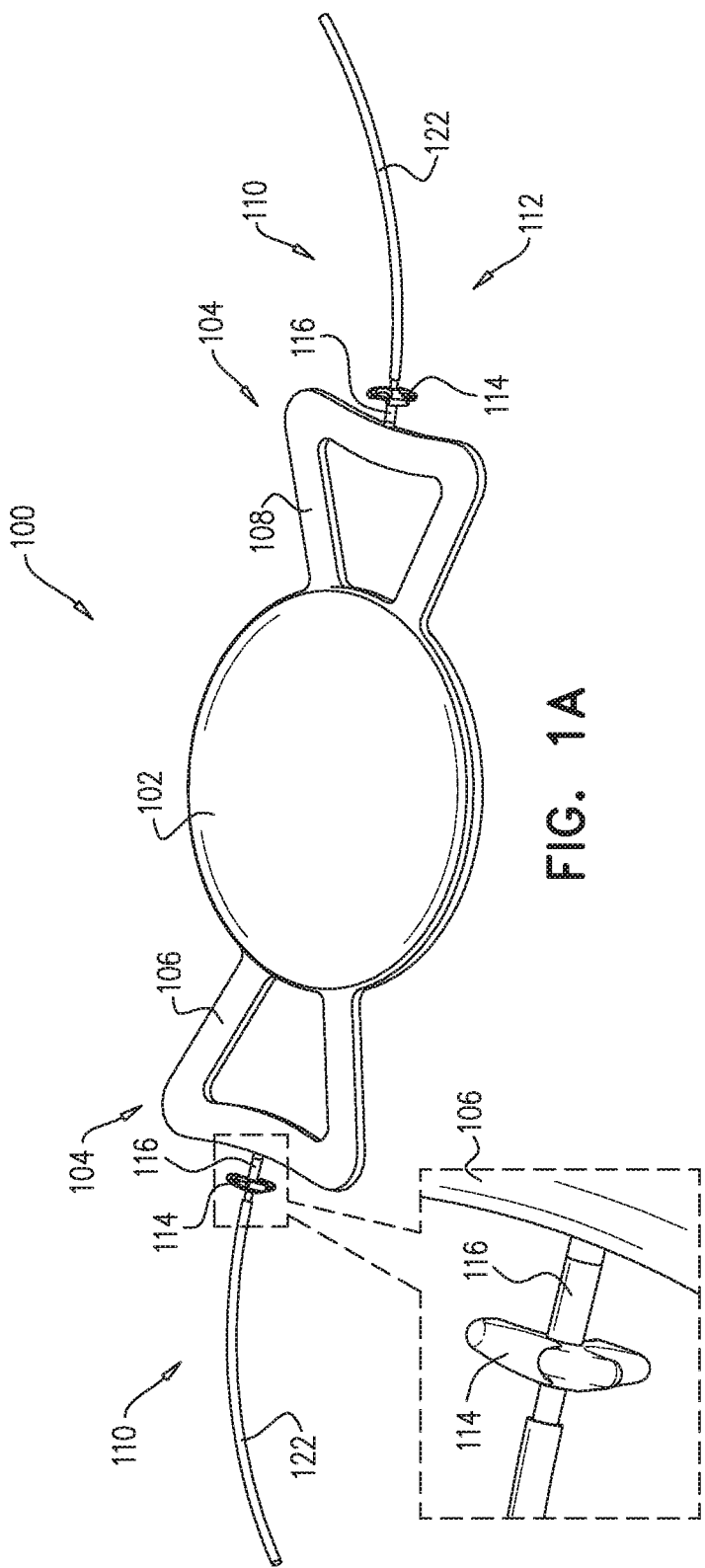

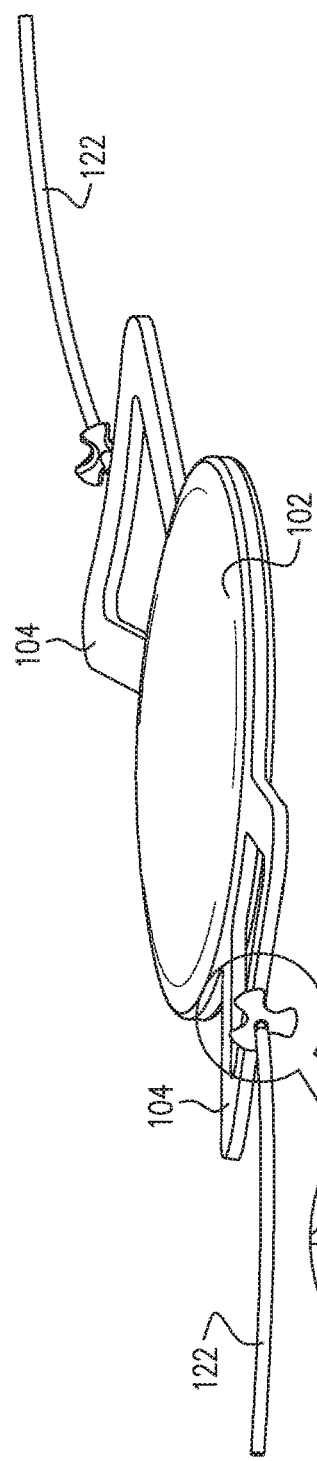
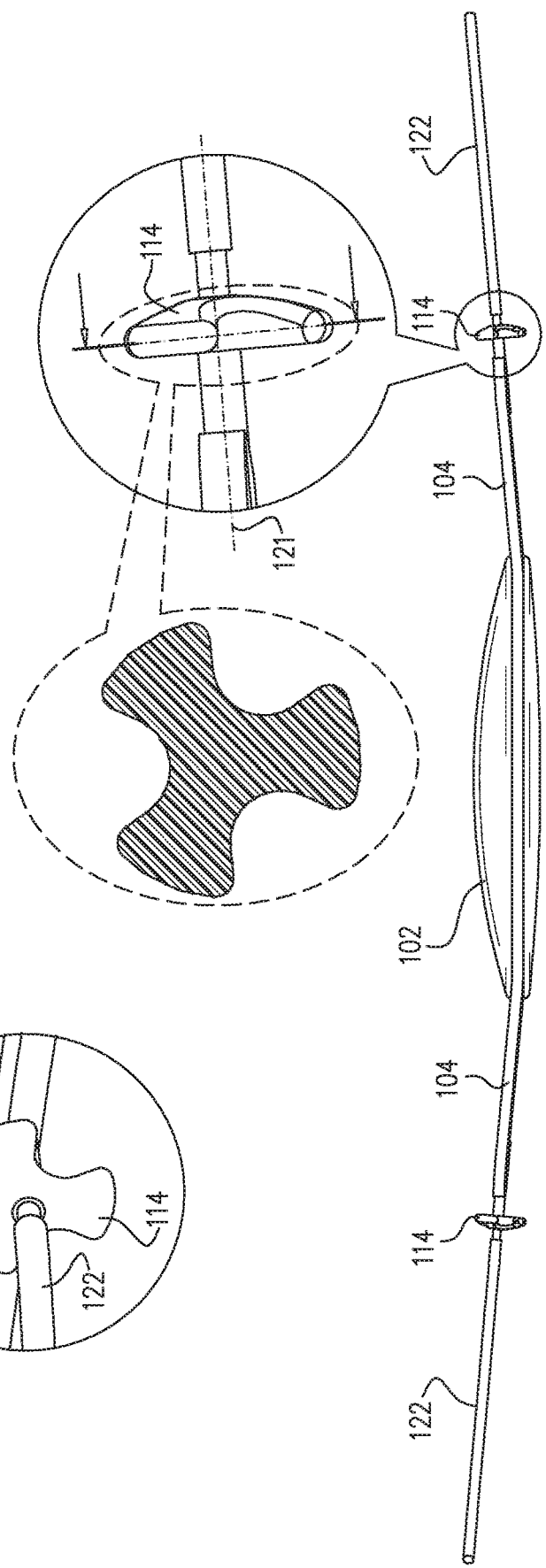

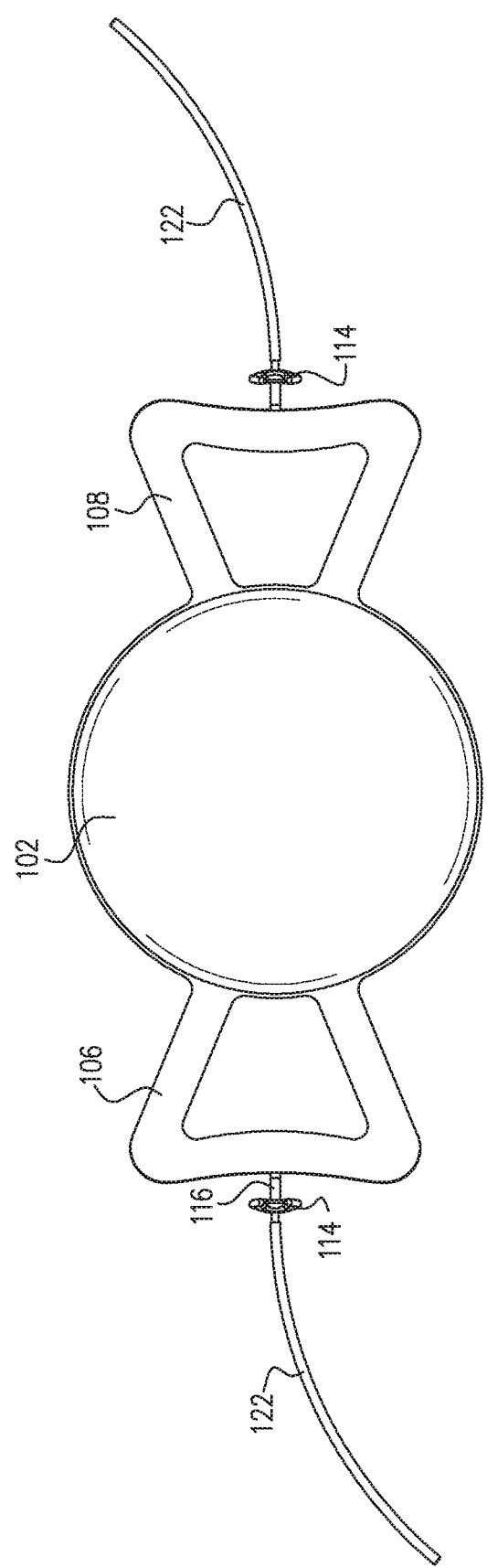

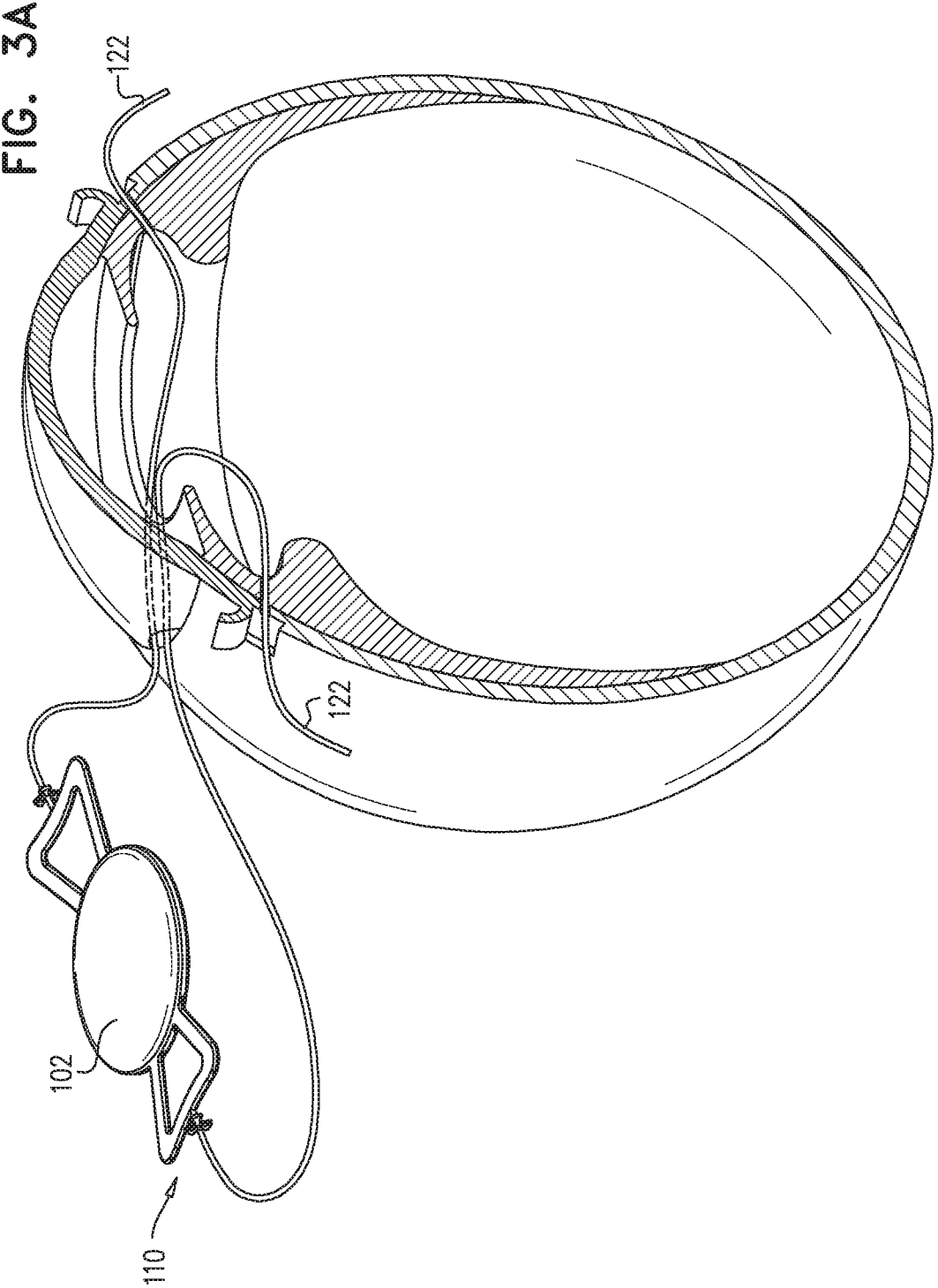

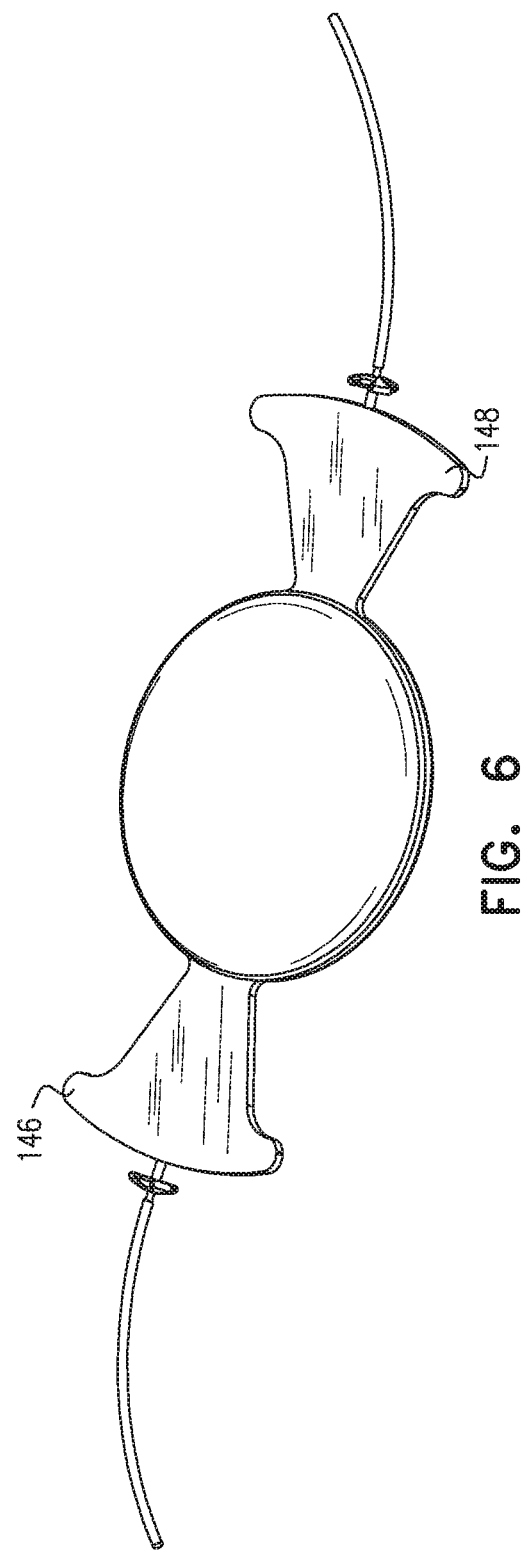

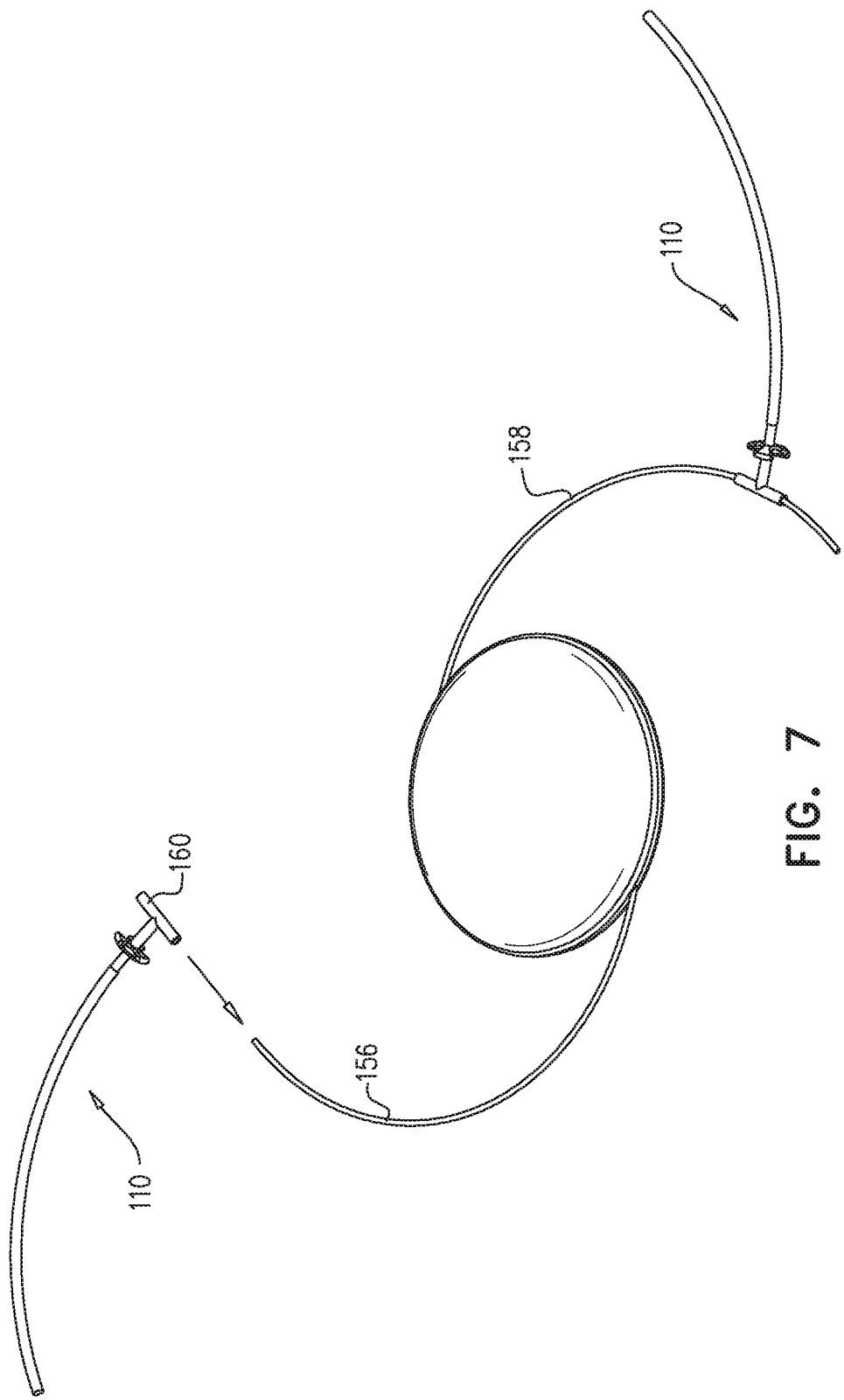

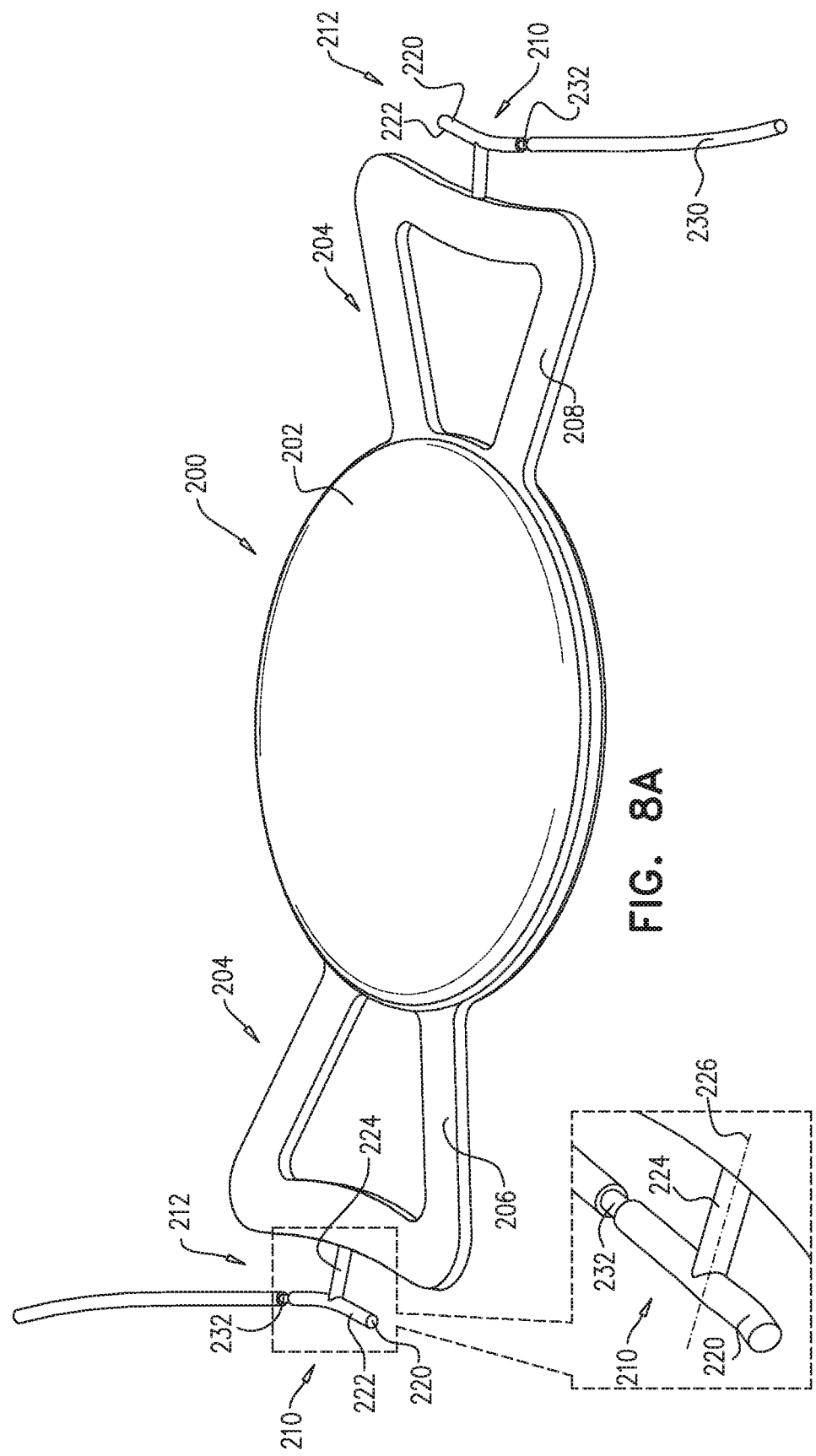

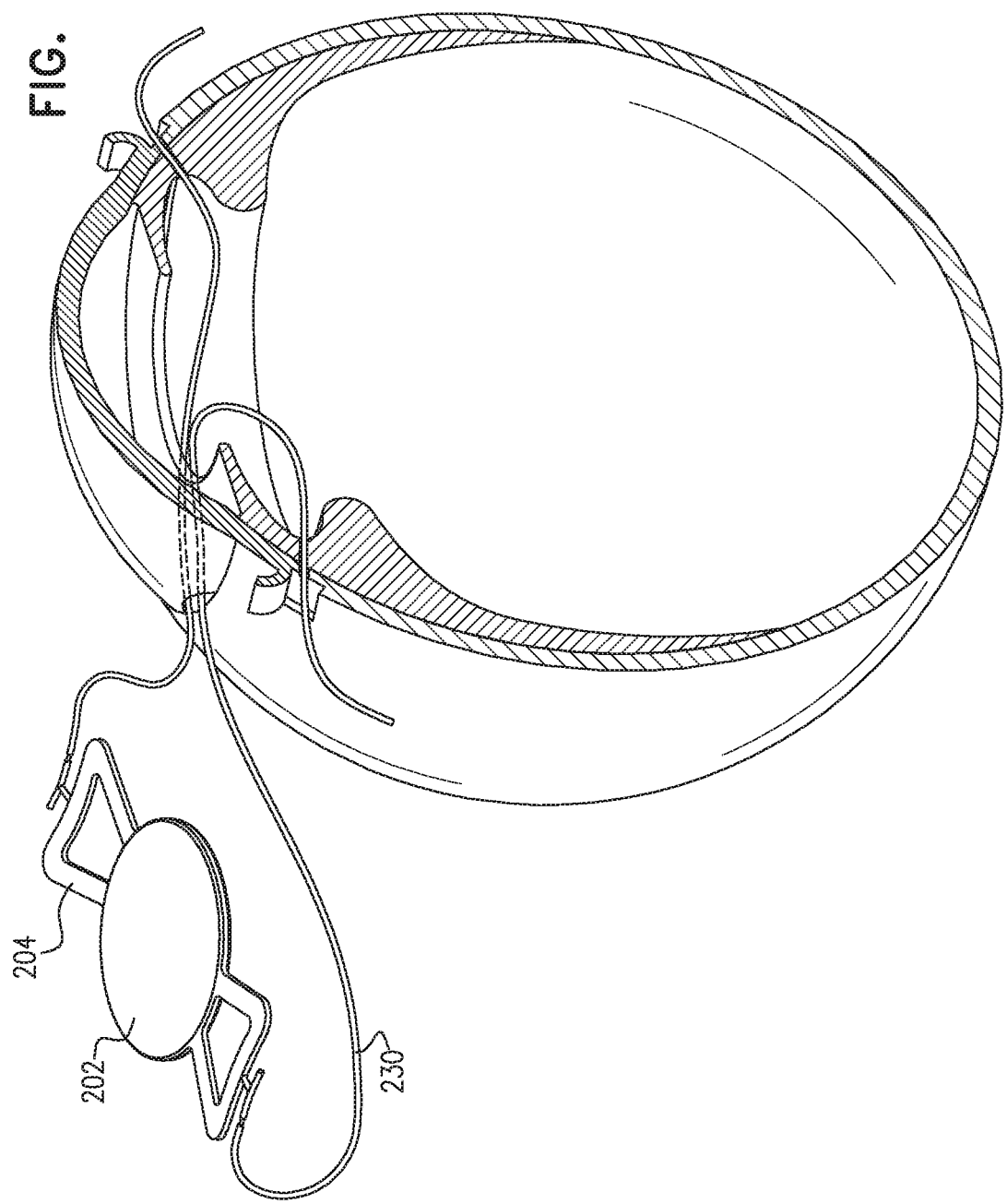

INTRAOCULAR LENS INCLUDING SCLERAL ENGAGEMENT PORTION

FIELD OF THE INVENTION

The present invention relates to intraocular lenses generally.

BACKGROUND OF THE INVENTION

Various types of intraocular lenses are known in the art.

SUMMARY OF THE INVENTION

The present invention seeks to provide an improved intraocular lens.

There is thus provided in accordance with a preferred embodiment of the present invention an intraocular lens including a lens portion and a haptics portion, the haptics portion including a scleral engagement portion including an elongate scleratomy transversing portion and a scleral engagement fixation portion, located at an intermediate location along a length of the elongate scleratomy transversing portion, preventing disengagement of the scleratomy transversing portion from a sclera.

Preferably, the scleral engagement fixation portion is configured to be bendable in a first direction along a central axis thereof but not to be bendable in a second direction along the central axis, opposite to the first direction.

In accordance with a preferred embodiment of the present invention, the scleral engagement fixation portion is configured to assume a relatively narrow footprint perpendicular to a central axis thereof during insertion thereof via a scleratomy and a relatively wide footprint perpendicular to the central axis for retaining the scleral engagement fixation portion against passing back through the scleratomy and thus retaining the intraocular lens in position in the eye.

Preferably, the scleral engagement fixation portion is in the form of a button. Additionally, the button is a multi-lobed button.

In accordance with a preferred embodiment of the present invention the scleral engagement fixation portion is in the form of part of a selectably bendable T-shaped element. Preferably, the T-shaped element includes a flexible base portion. In accordance with a preferred embodiment of the present invention the flexible base portion is formed of suture material.

In accordance with a preferred embodiment of the present invention the lens portion and the haptics portion are integrally formed as one piece.

Preferably, the elongate scleratomy transversing portion includes a threading portion extending beyond the scleral engagement fixation portion, which is adapted to be detached from the scleral engagement fixation portion following insertion of the intraocular lens and discarded.

BRIEF DESCRIPTION OF THE DRAWINGS

The present invention will be understood and appreciated more fully from the following detailed description, taken in conjunction with the drawings in which:

FIGS. 1A, 1B and 1C are first, second and third different simplified perspective views of an intraocular lens constructed and operative in accordance with a preferred embodiment of the present invention;

FIGS. 1D and 1E are respectively a simplified side view and a simplified top view illustration of the intraocular lens of FIGS. 1A, 1B & 1C;

FIGS. 3A and 3B are simplified views of the intraocular lens of FIGS. 1A-2C in respective pre-insertion and post insertion operative orientations;

FIG. 6 is a simplified pictorial illustration of an intraocular lens constructed and operative in accordance with yet another preferred embodiment of the present invention;

FIG. 7 is a simplified pictorial illustration of an intraocular lens constructed and operative in accordance with still another preferred embodiment of the present invention;

FIGS. 8A, 8B and 8C are first, second and third different simplified perspective views of an intraocular lens constructed and operative in accordance with a further preferred embodiment of the present invention;

FIGS. 10A and 10B are simplified views of the intraocular lens of FIGS. 8A-9 in respective pre-insertion and post insertion operative orientations;

DETAILED DESCRIPTION OF PREFERRED EMBODIMENTS

Figure 1B:
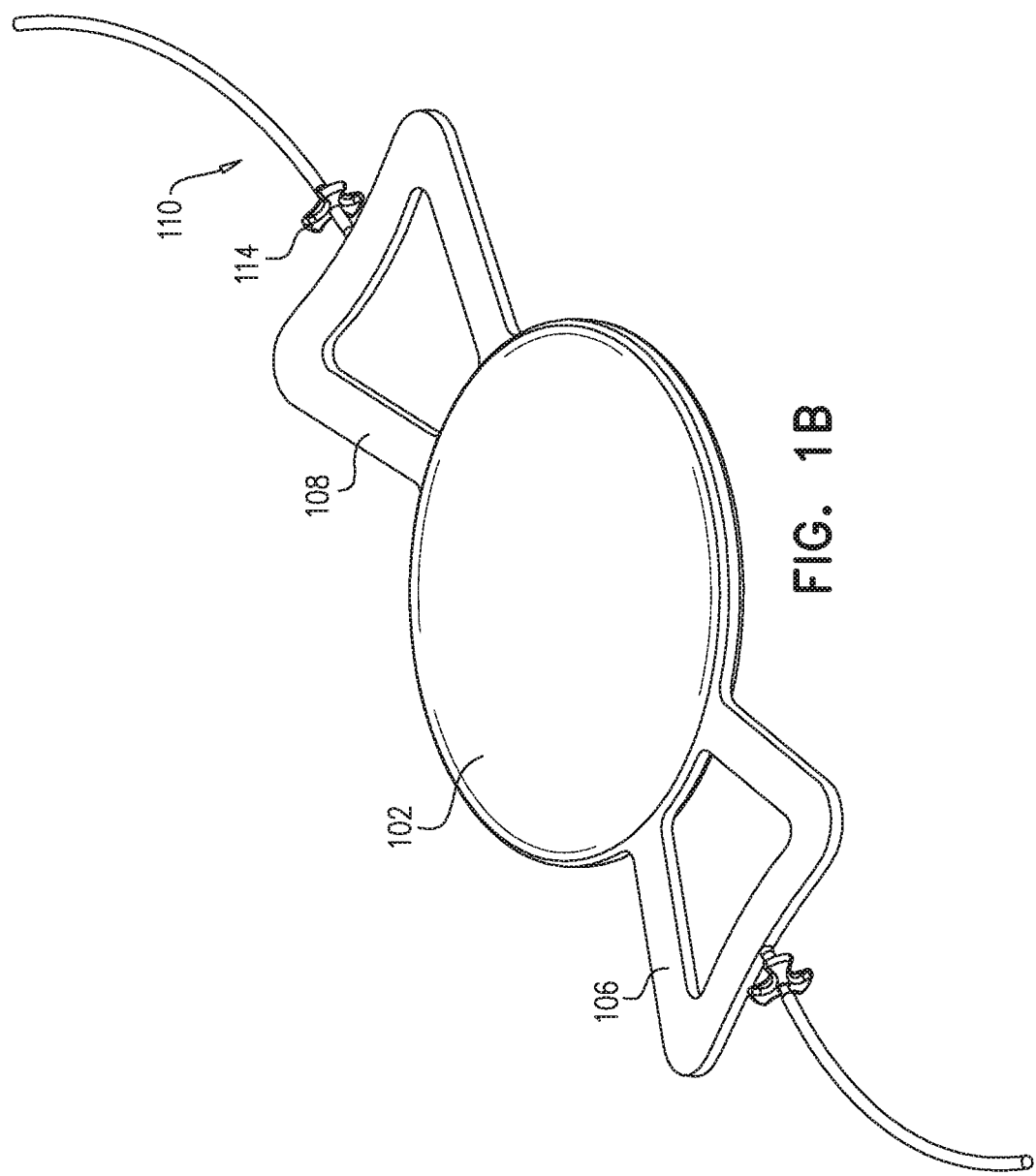

Reference is now made to FIGS. 1A, 1B and 1C, which are first, second and third different simplified perspective views of an intraocular lens constructed and operative in accordance with a preferred embodiment of the present invention, and to FIGS. 1D and 1E, which are, respectively, a simplified side view and a simplified top view illustration of the intraocular lens of FIGS. 1A, 1B & 1C.

As seen in FIGS. 1A-1E, there is provided an intraocular lens 100, constructed and operative in accordance with a preferred embodiment of the present invention, which includes a lens portion 102 and haptics portions 104. Haptics portion 104 preferably includes first and second side haptics 106 and 108 extending outwardly from lens portion 102. A scleral engagement portion 110 extends outwardly from each of side haptics 106 and 108 at a location intermediate therealong. Each scleral engagement portion 110 preferably includes a scleratomy transversing portion 112, preferably in the form of an elongate flexible thread, which may be formed of suture material, and a scleral engagement fixation portion 114, at a location intermediate along scleratomy transversing portion 112, preventing disengagement of the scleratomy transversing portion 112 from a sclera.

In this embodiment, the scleral engagement fixation portion 114 is generally in the form of a button which is configured to be bendable in a first direction along a base portion 116 defining a central axis 121 thereof, for scleral engagement, but not in an opposite direction, for scleral engagement fixation, as will be described hereinbelow in greater detail. Thus, the scleral engagement fixation portion 114 can assume a relatively small footprint perpendicular to axis 121 during insertion thereof via a scleratomy and a relatively large footprint perpendicular to axis 121 for retaining the scleral engagement fixation portion 114 against passing back through the scleratomy and thus retaining the intraocular lens 100 in position in the eye.

Preferably, scleratomy transversing portion 112 includes a scleratomy threading portion 122, extending outwardly of each scleral engagement fixation portion 114, which is used for insertion and is subsequently cut off from the scleral engagement fixation portion 114 and discarded.

It is appreciated that all parts of the intraocular lens 100 described above may be integrally formed as a single piece. Alternatively, various portions of the intraocular lens 100 may be formed separately and joined together by conventional welding techniques or the use of suitable adhesives.

Figure 2A:
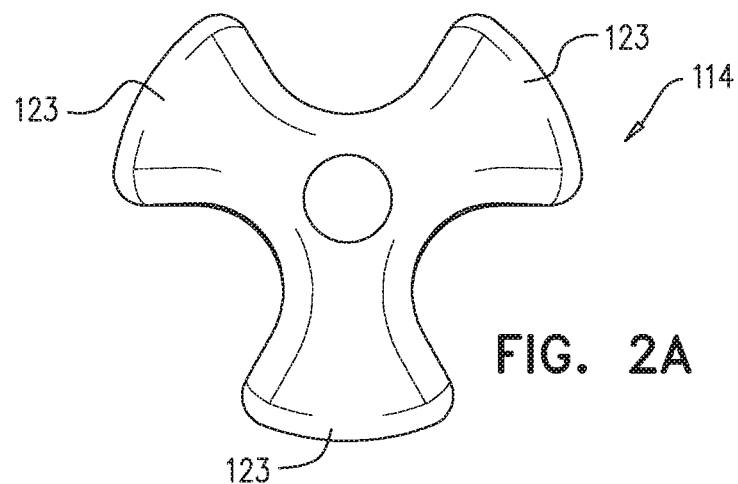
FIGS. 2A, 2B and 2C are three simplified views of a button portion of the intraocular lens of FIGS. 1A-1E.
Figure 2B:
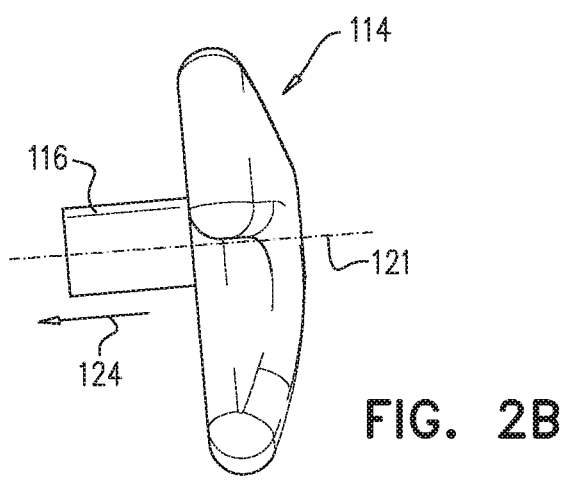
Figure 2C:
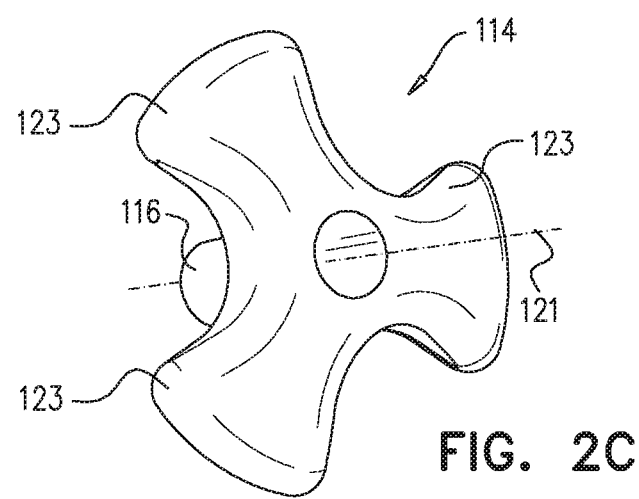
Figure 3B:
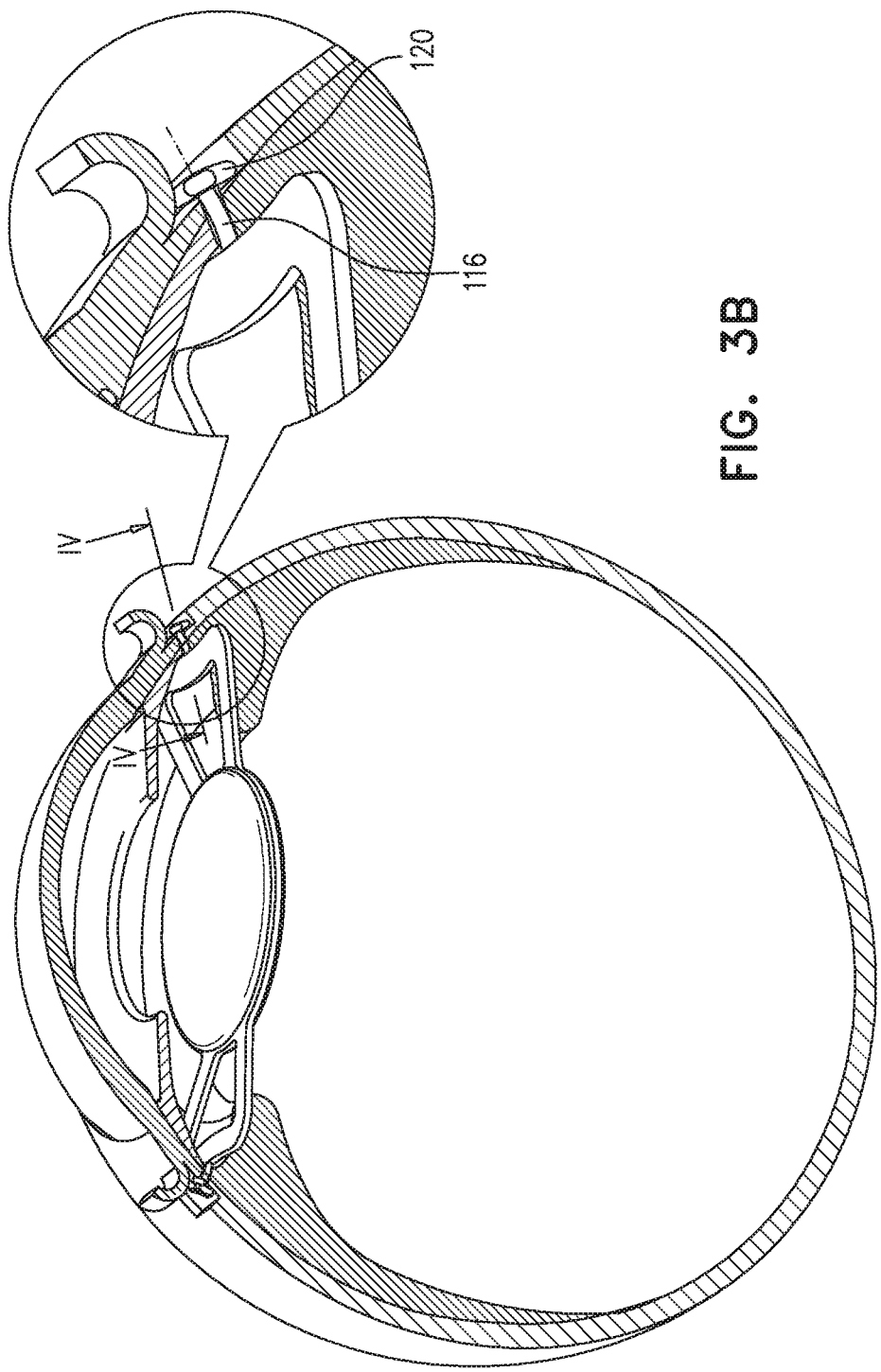
Figure 4A:
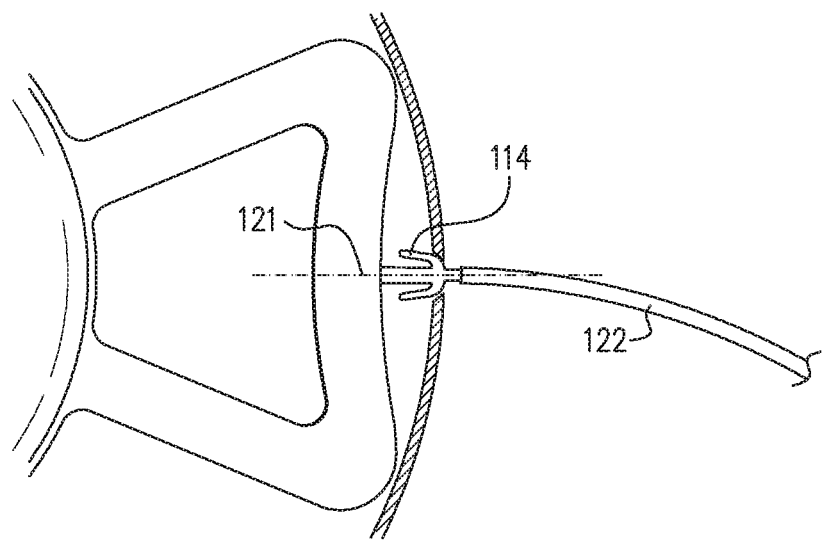
FIGS. 4A, 4B and 4C are simplified views of three intermediate stages in the insertion of the intraocular lens of FIGS. 1A-3B, taken along lines IV-IV in FIG. 3B.
Figure 4B:
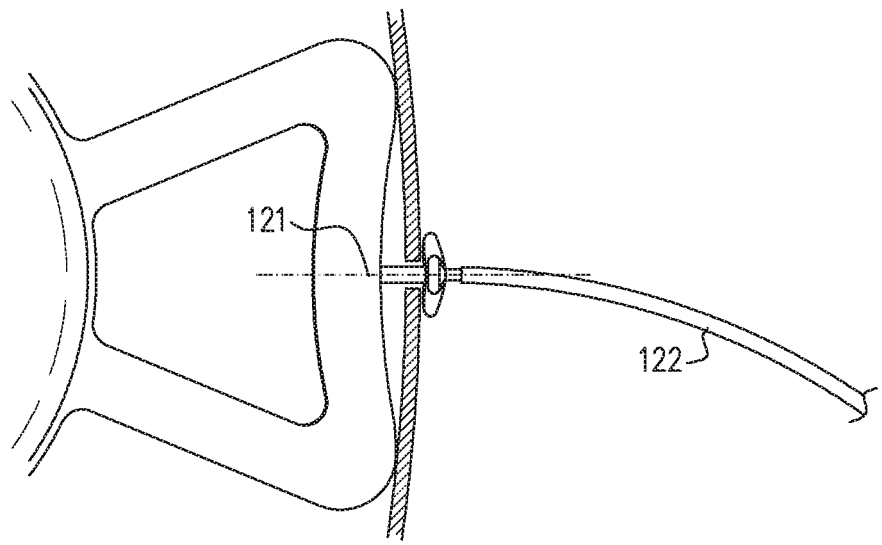
Figure 4C:
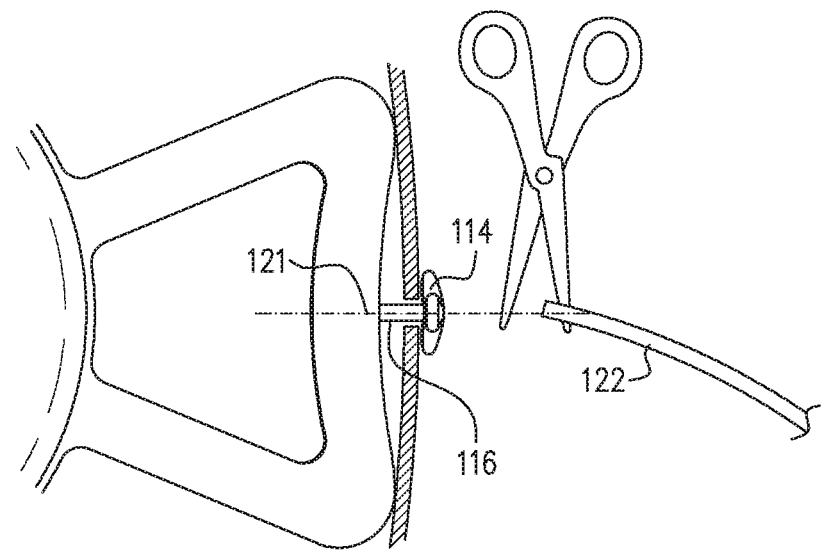

Reference is now made to FIGS. 2A, 2B and 2C, which are three simplified views of a scleral engagement fixation portion of the intraocular lens of FIGS. 1A-1E, to FIGS. 3A and 3B, which are simplified views of the intraocular lens of FIGS. 1A-2C in respective pre-insertion and post insertion operative orientations, and to FIGS. 4A, 4B and 4C, which are simplified views of three intermediate stages in the insertion of the intraocular lens of FIGS. 1A-3B.

As seen particularly in FIGS. 2A-2C, the scleral engagement fixation portion 114 is preferably shaped as a multilobed button, including two or more lobes 123, which is configured to be bendable in a first direction, indicated by arrow 124, along central axis 121 thereof over scleratomy transversing portion 112, during insertion, as seen in FIG. 4A, but not in a second direction, opposite to the first direction 124 along axis 121, over scleratomy threading portion 122, thereby to retain the intraocular lens in place as shown in FIGS. 3B and 4B.

As seen in FIG. 4C, following insertion of intraocular lens 100, scleratomy threading portion 122 extending outwardly of each scleral engagement fixation portion 114 is cut off from the scleral engagement fixation portion 114 and discarded.

Figure 5:
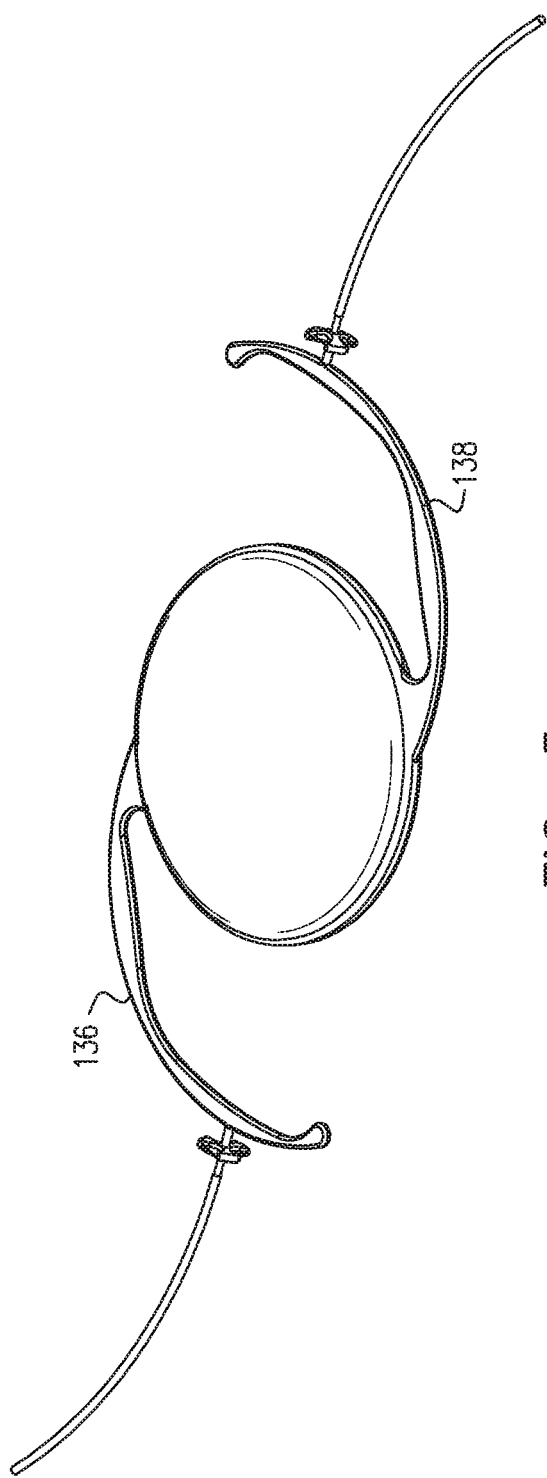
FIG. 5 is a simplified pictorial illustration of an intraocular lens constructed and operative in accordance with another preferred embodiment of the present invention.

Reference is now made to FIG. 5, which is a simplified pictorial illustration of an intraocular lens constructed and operative in accordance with another preferred embodiment of the present invention, wherein articulated side haptics portions 136 and 138 are employed.

Reference is now made to FIG. 6, which is a simplified pictorial illustration of an intraocular lens constructed and operative in accordance with yet another preferred embodiment of the present invention, wherein solid side haptics portions 146 and 148 are employed.

Reference is now made to FIG. 7, which is a simplified pictorial illustration of an intraocular lens constructed and operative in accordance with yet another preferred embodiment of the present invention, wherein elongate threadlike side haptics portions 156 and 158 are employed and may each be connected, as by a coupler 160, to scleral engagement portion 110.

Figure 8B:
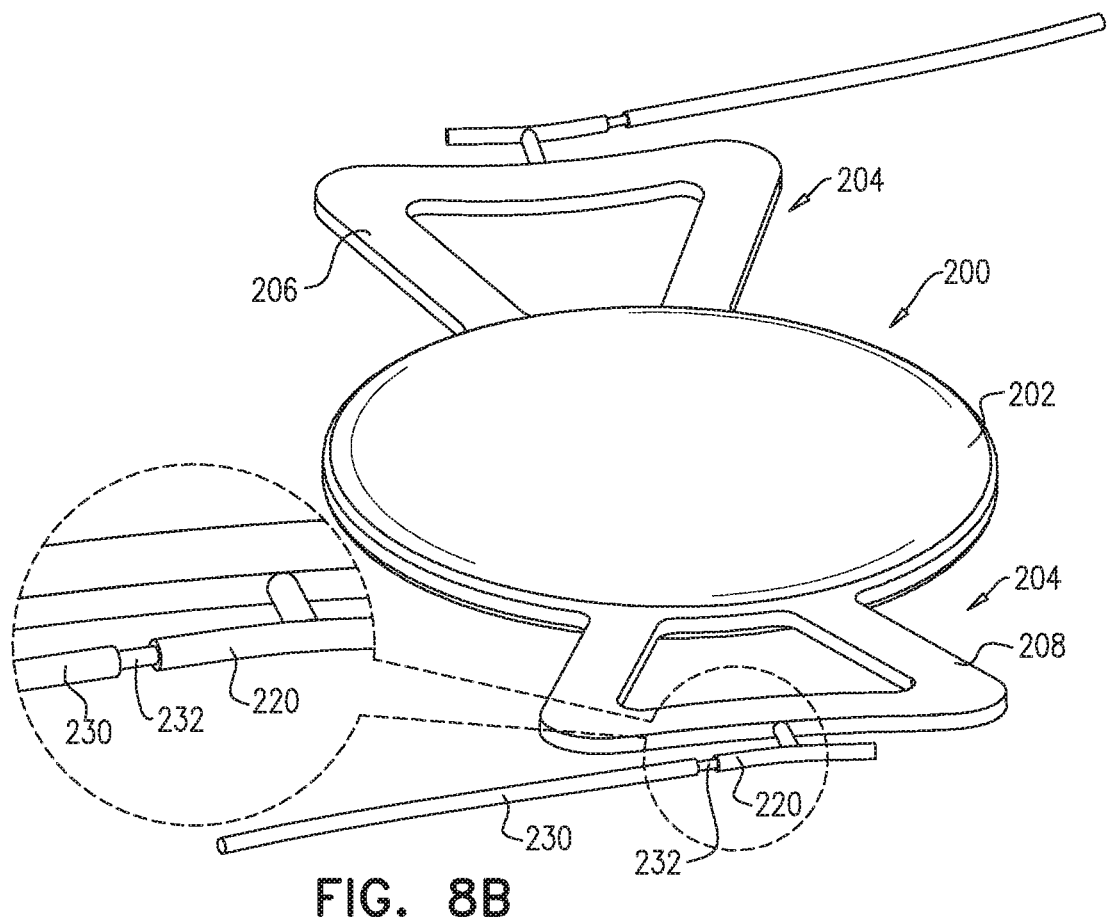
Figure 8C:
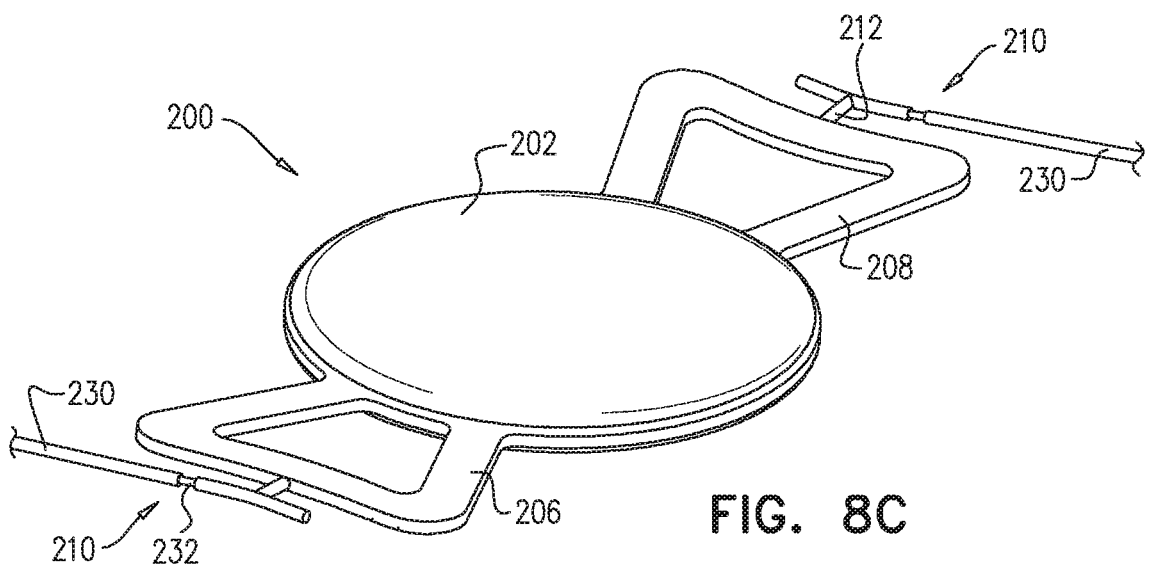
Figure 8D:
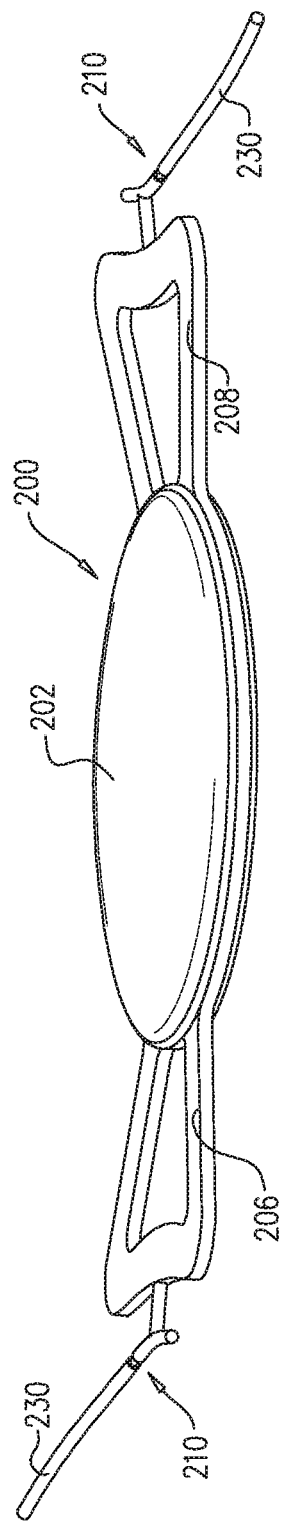
FIGS. 8D and 8E are, respectively, a simplified side view and a simplified top view illustration of the intraocular lens of FIGS. 8A, 8B & 8C.
Figure 8E:
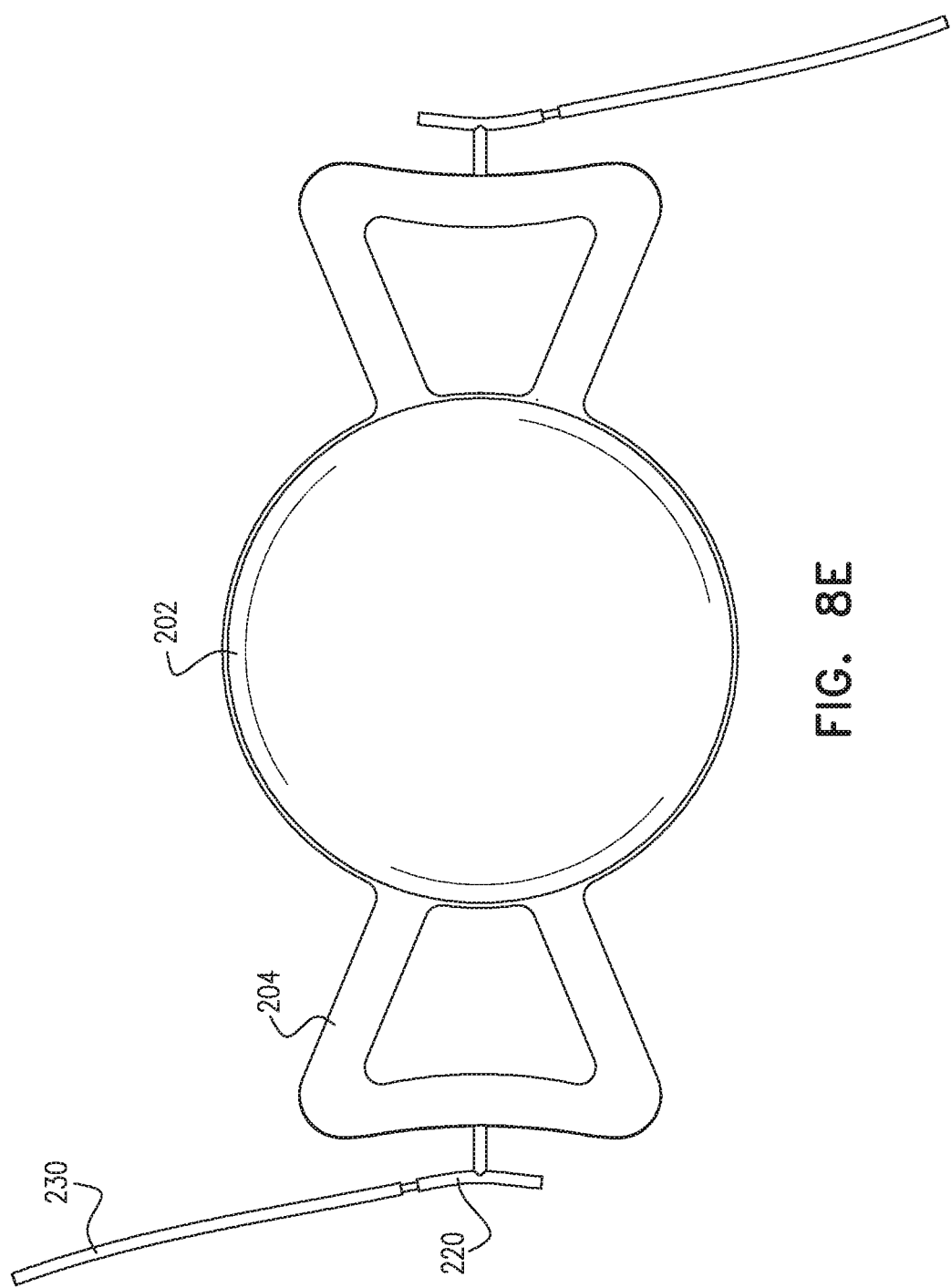

Reference is now made to FIGS. 8A, 8B and 8C, which are first, second and third different simplified perspective views of an intraocular lens constructed and operative in accordance with another preferred embodiment of the present invention, and to FIGS. 8D and 8E, which are, respectively, a simplified side view and a simplified top view illustration of the intraocular lens of FIGS. 8A-8C.

As seen in FIGS. 8A-8E, there is provided an intraocular lens 200, constructed and operative in accordance with a preferred embodiment of the present invention, which includes a lens portion 202 and haptics portions 204. Haptics portions 204 preferably includes first and second side haptics 206 and 208 extending outwardly from lens portion 202. A scleral engagement portion 210 extends outwardly from each of side haptics 206 and 208. Each scleral engagement portion 210 preferably includes a scleratomy transversing portion 212, preferably in the form of an elongate flexible thread, having a scleral engagement fixation portion 220 at a location intermediate along scleratomy transversing portion 212, preventing disengagement of the scleral transversing portion 212 from a sclera.

In this embodiment, the scleral engagement fixation portion 220 is in the form of a generally T-shaped element 222 which is configured to be selectably bendable during insertion of intraocular lens 200 and to provide for scleral engagement fixation, as will be described hereinbelow in greater detail.

In the illustrated embodiment, a flexible base portion 224 of the T-shaped element 222 extends along central axis 226 and defines part of the scleratomy transversing portion 212. In a preferred embodiment, flexible base portion 224 is formed of a soft, flexible material such as suture material. A free end 228 of each base portion 224 is joined to a corresponding one of side haptics 206 and 208. It is appreciated that the scleral engagement fixation portion 220 can assume a relatively narrow footprint perpendicular to axis 224 during insertion thereof via a scleratomy and a relatively wide footprint perpendicular to axis 224 for retaining the scleral engagement fixation portion 220 against passing back through the scleratomy and thus retaining the intraocular lens 200 in position in the eye. Preferably, a scleratomy threading portion 230 defines a further portion of the scleratomy transversing portion 212 and extends outwardly of one side of each T-shaped element 222. Preferably, the scleratomy threading portion 230 is used for threading the scleratomy transversing portion 212 through the sclera and is subsequently cut off from the scleral engagement fixation portion 220, at a narrowed and weakened portion 232 thereof, at which the scleratomy threading portion 230 is joined to the T-shaped element 222, and discarded.

It is appreciated that all parts of the intraocular lens 200 described above may be integrally formed as a single piece. Alternatively, various portions of the intraocular lens 200 may be formed separately and joined together by conventional welding techniques or the use of suitable adhesives.

Figure 9A:
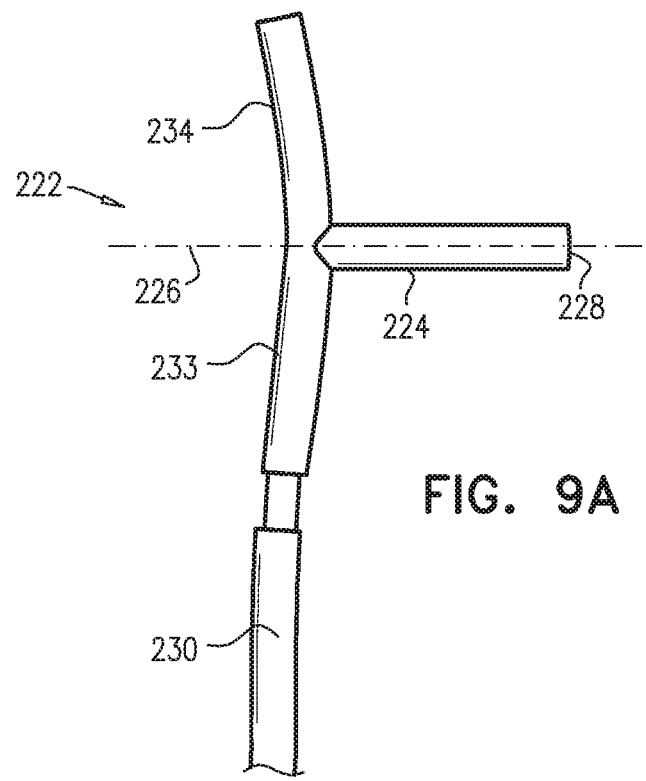
FIGS. 9A and 9B are simplified views of a T-shaped element of the intraocular lens of FIGS. 8A-8E.
Figure 9B:
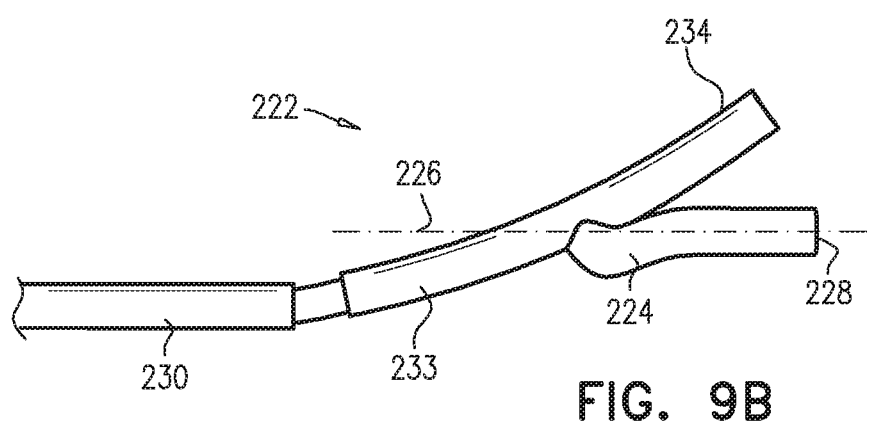

Reference is now made to FIGS. 9A and 9B, which are simplified views of T-shaped element 222 of the intrarocular lens of FIGS. 8A-8E, to FIGS. 10A and 10B, which are simplified views of the intraocular lens of FIGS. 8A-9 in respective pre-insertion and post insertion operative orientations, and to FIGS. 11A, 11B, 11C and 11D, which are simplified views of four intermediate stages in the insertion of the intraocular lens of FIGS. 8A-10B.

Figure 10B:
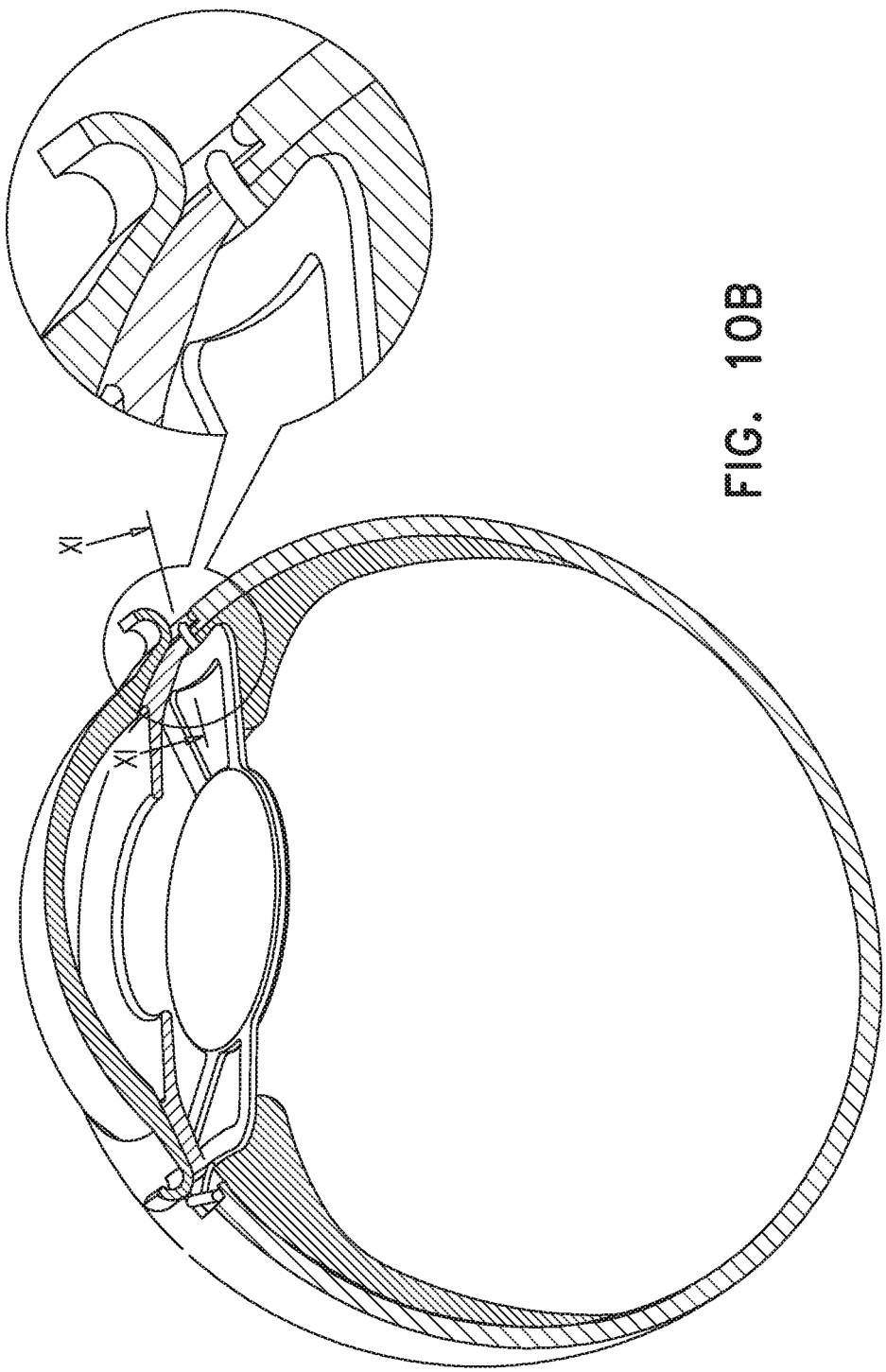
Figure 11A:
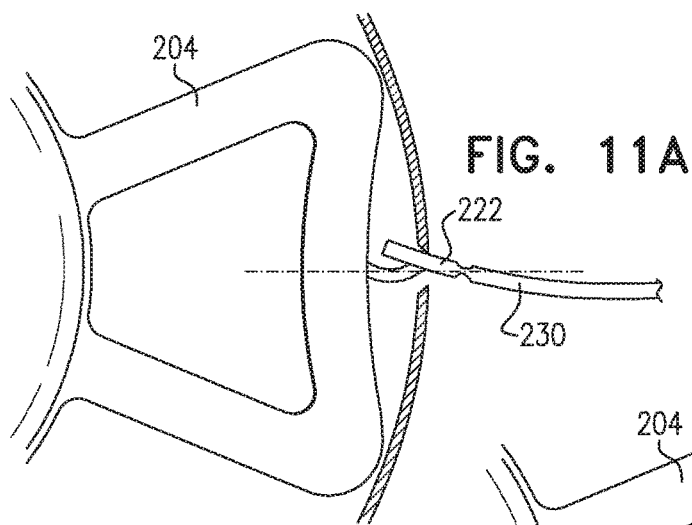
FIGS. 11A, 11B, 11C and 11D are simplified views of four intermediate stages in the insertion of the intraocular lens of FIGS. 8A-10B, taken along lines XI-XI in FIG. 10B.
Figure 11B:
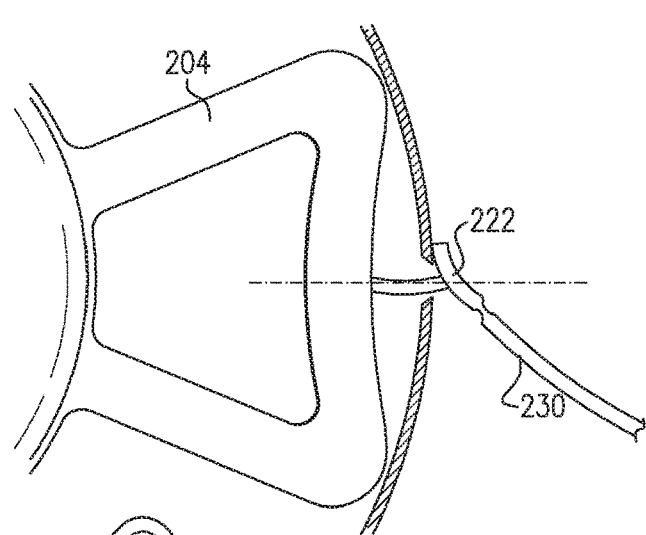
Figure 11C:
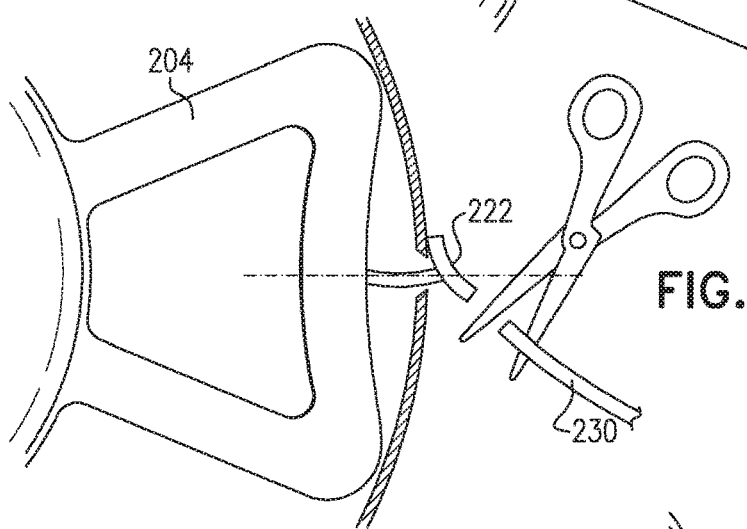
Figure 11D:
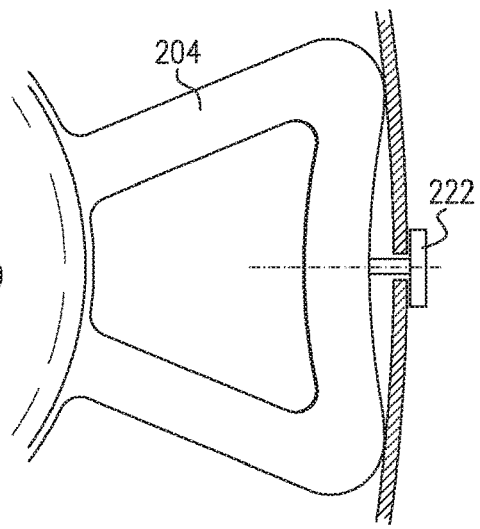

As seen particularly in FIGS. 9A and 9B, the scleral engagement fixation portion 220 is preferably shaped as a pair of coaxial oppositely directed arms 233 and 234 of generally T-shaped element 222, which is configured to be selectably bendable, from the configuration shown in FIG. 9A to the configuration shown in FIG. 9B, during insertion of intraocular lens 200, as seen in FIGS. 10A-11D, and to retain the intraocular lens in place, following insertion thereof, as shown in FIGS. 10B and 11D.

Figure 12:
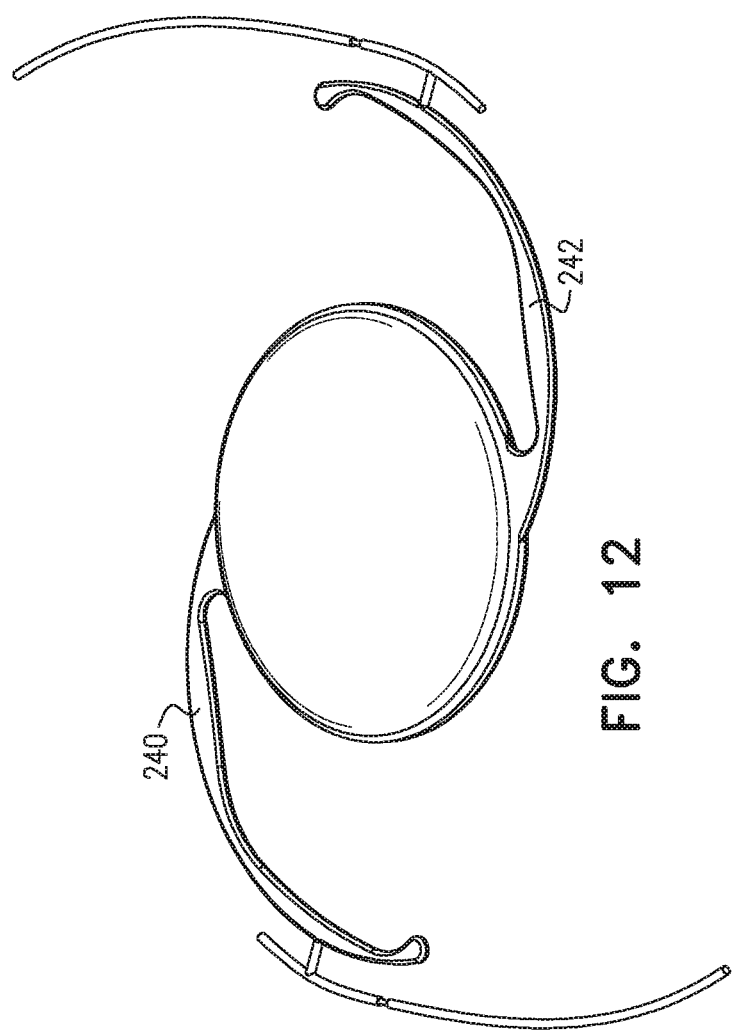
FIG. 12 is a simplified pictorial illustration of an intraocular lens constructed and operative in accordance with another preferred embodiment of the present invention.

Reference is now made to FIG. 12, which is a simplified pictorial illustration of an intraocular lens constructed and operative in accordance with another preferred embodiment of the present invention, wherein articulated side haptics portions 240 and 242 are employed.

Figure 13:
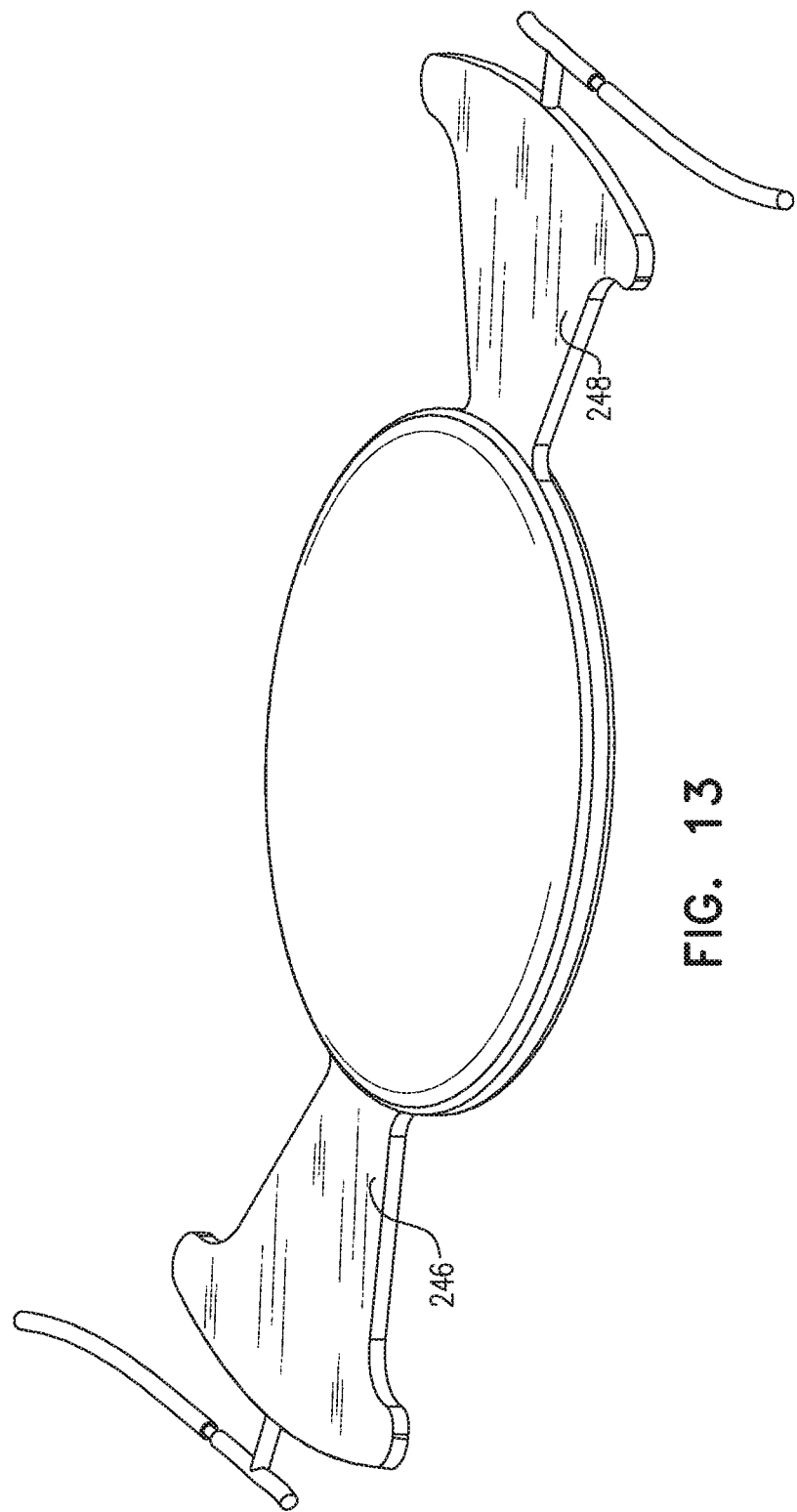
FIG. 13 is a simplified pictorial illustration of an intraocular lens constructed and operative in accordance with yet another preferred embodiment of the present invention.

Reference is now made to FIG. 13, which is a simplified pictorial illustration of an intraocular lens constructed and operative in accordance with yet another preferred embodiment of the present invention, wherein solid side haptics portions 246 and 248 are employed.

Figure 14:
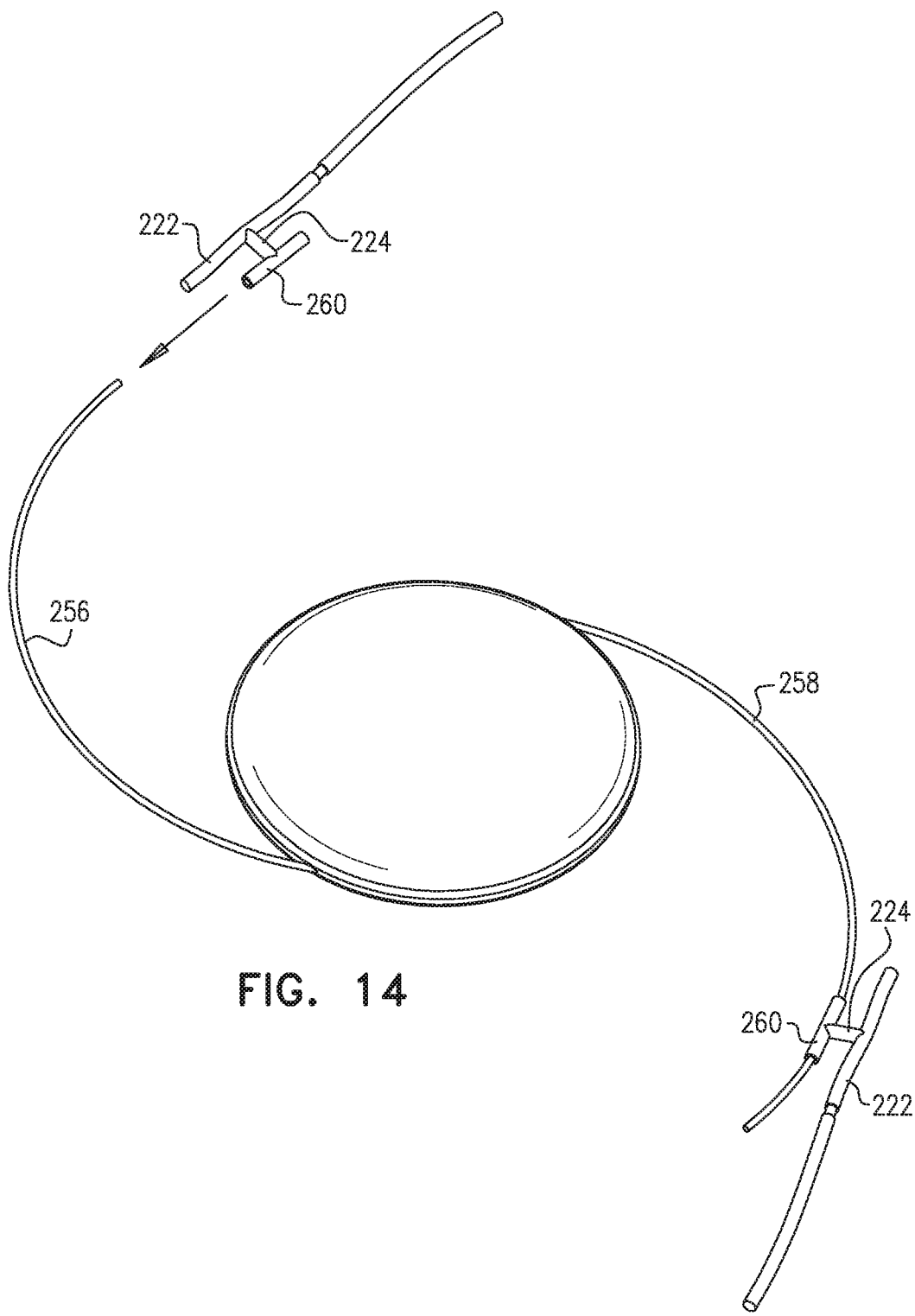
FIG. 14 is a simplified pictorial illustration of an intraocular lens constructed and operative in accordance with still another preferred embodiment of the present invention.

Reference is now made to FIG. 14, which is a simplified pictorial illustration of an intraocular lens constructed and operative in accordance with yet another preferred embodiment of the present invention, wherein elongate threadlike side haptics portions 256 and 258 are employed and may each be inserted into a hollow coupler 260 connected to base 226 of T-shaped element 222.

It will be appreciated by persons skilled in the art that the present invention is not limited by what has been specifically shown and described hereinabove. Rather the scope of the present invention includes both combinations and subcombinations of the various elements described hereinabove as well as modifications and variations thereof which are not in the prior art.

The invention claimed is:

1. An intraocular lens comprising:
a lens portion; and
a haptics portion, said haptics portion including a scleral engagement portion including an elongate scleratomy transversing portion and a scleral engagement fixation portion, located at an intermediate location along a length of said elongate scleratomy transversing portion, preventing disengagement of said scleratomy transversing portion from a sclera,
said scleral engagement fixation portion being configured to assume a relatively narrow footprint perpendicular to a central axis thereof during insertion thereof via a scleratomy and a relatively wide footprint perpendicular to said central axis for retaining the scleral engagement fixation portion against passing back through the scleratomy and thus retaining said intraocular lens in position in the eye,
said elongate scleratomy transversing portion comprising a threading portion, extending beyond said scleral engagement fixation portion, which is used for insertion of said intraocular lens and is adapted to be detached from said scleral engagement fixation portion following insertion of said intraocular lens and discarded.

2. An intraocular lens according to claim 1 and wherein said scleral engagement fixation portion is in the form of a button.

3. An intraocular lens according to claim 2 and wherein said button is a multi-lobed button.

4. An intraocular lens according to claim 1 and wherein said scleral engagement fixation portion is in the form of part of a selectably bendable T-shaped element.

5. An intraocular lens according to claim 4 and wherein said T-shaped element includes a flexible base portion.

6. An intraocular lens according to claim 5 and wherein said flexible base portion is formed of suture material.

7. An intraocular lens according to claim 1 and wherein said lens portion and said haptics portion are integrally formed as one piece.

8. An intraocular lens comprising:
a lens portion; and
a haptics portion, said haptics portion including a scleral engagement portion including an elongate scleratomy transversing portion and a scleral engagement fixation portion, located at an intermediate location along a length of said elongate scleratomy transversing portion, preventing disengagement of said scleratomy transversing portion from a sclera,
said scleral engagement fixation portion being configured to be bendable in a first direction along a central axis thereof but not to be bendable in a second direction along said central axis, opposite to said first direction,
said elongate scleratomy transversing portion comprising a threading portion, extending beyond said scleral engagement fixation portion, which is used for insertion of said intraocular lens and is adapted to be detached from said scleral engagement fixation portion following insertion of said intraocular lens and discarded.

9. An intraocular lens according to claim 8 and wherein said scleral engagement fixation portion is configured to assume a relatively narrow footprint perpendicular to a central axis thereof during insertion thereof via a scleratomy and a relatively wide footprint perpendicular to said central axis for retaining the scleral engagement fixation portion against passing back through the scleratomy and thus retaining said intraocular lens in position in the eye.

10. An intraocular lens according to claim 8 and wherein said scleral engagement fixation portion is in the form of a button.

11. An intraocular lens according to claim 10 and wherein said button is a multi-lobed button.

12. An intraocular lens according to claim 8 and wherein said lens portion and said haptics portion are integrally formed as one piece.

* * * * *